US009377443B2

(12) United States Patent
Kessler et al.

(10) Patent No.: US 9,377,443 B2
(45) Date of Patent: *Jun. 28, 2016

(54) SCANNING ACOUSTIC MICROSCOPE WITH AN INVERTED TRANSDUCER AND BUBBLER FUNCTIONALITY

(71) Applicant: Sonoscan, Inc., Elk Grove Village, IL (US)

(72) Inventors: Lawrence W. Kessler, Buffalo Grove, IL (US); Thomas Kleinschmidt, Prospect Heights, IL (US); Dan Micek, Norridge, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/216,429

(22) Filed: Mar. 17, 2014

(65) Prior Publication Data

US 2014/0196543 A1 Jul. 17, 2014

Related U.S. Application Data

(63) Continuation of application No. 13/304,070, filed on Nov. 23, 2011, now Pat. No. 8,720,273.

(60) Provisional application No. 61/416,610, filed on Nov. 23, 2010.

(51) Int. Cl.
*G01N 29/06* (2006.01)
*G01N 29/28* (2006.01)
*G01N 29/265* (2006.01)

(52) U.S. Cl.
CPC .......... *G01N 29/0681* (2013.01); *G01N 29/265* (2013.01); *G01N 29/28* (2013.01); *G01N 2291/101* (2013.01); *G01N 2291/2697* (2013.01)

(58) Field of Classification Search
CPC .................. G01N 29/28; G01N 29/0681
USPC ................................... 73/606, 644
See application file for complete search history.

(56) References Cited

U.S. PATENT DOCUMENTS

| 3,762,591 | A | 10/1973 | Gray |
| 4,021,771 | A | 5/1977 | Collins et al. |
| 4,455,872 | A | 6/1984 | Kossoff et al. |
| 4,518,992 | A | 5/1985 | Kessler et al. |
| 4,768,155 | A | 8/1988 | Takishita et al. |
| 4,781,067 | A | 11/1988 | Cichanski |
| 4,866,986 | A | 9/1989 | Cichanski |

(Continued)

OTHER PUBLICATIONS

U.S. Appl. No. 61/362,131, Inventors Lawrence Kessler et al.;, filed Jul. 7, 2010, (9 pages).

(Continued)

*Primary Examiner* — J M Saint Surin
(74) *Attorney, Agent, or Firm* — McCracken & Gillen LLC

(57) ABSTRACT

A scanning acoustic microscope includes a transducer mounted in a cup below a particular elevation capable of producing ultrasonic energy and a coupling fluid source disposed below the particular elevation, which is configured to introduce coupling fluid into the cup. Ultrasonic energy is directed upwardly through coupling fluid disposed between and contacting the transducer and a first surface of a part to be inspected. The part is disposed at the particular elevation such that a second surface of the part is not contacted by coupling fluid during testing.

20 Claims, 2 Drawing Sheets

(56) References Cited

U.S. PATENT DOCUMENTS

| | | |
|---|---|---|
| 4,995,259 A | 2/1991 | Khuri-Yakub et al. |
| 5,351,544 A | 10/1994 | Endo et al. |
| 5,600,068 A | 2/1997 | Kessler et al. |
| 5,602,336 A | 2/1997 | Takeuchi et al. |
| 5,684,252 A | 11/1997 | Kessler et al. |
| 5,714,756 A | 2/1998 | Park et al. |
| 6,357,136 B1 | 3/2002 | Erickson et al. |
| 6,460,414 B1 | 10/2002 | Erickson et al. |
| 6,880,387 B2 | 4/2005 | Kessler et al. |
| 6,890,302 B2 | 5/2005 | Oravecz et al. |
| 6,895,820 B2 | 5/2005 | Oravecz et al. |
| 6,912,908 B2 | 7/2005 | Kessler et al. |
| 6,981,417 B1 | 1/2006 | Oravecz |
| 7,000,475 B2 | 2/2006 | Oravecz et al. |
| 7,104,132 B2 | 9/2006 | Mueller |
| 7,395,713 B2 | 7/2008 | Kessler et al. |
| 7,522,780 B2 | 4/2009 | Oravecz et al. |
| 7,530,271 B2 | 5/2009 | Busch et al. |
| 7,584,664 B2 | 9/2009 | Kessler |
| 7,661,315 B2 | 2/2010 | Busch et al. |
| 8,720,273 B2 * | 5/2014 | Kessler .................. G01N 29/28 73/606 |
| 9,170,236 B2 * | 10/2015 | Kessler .............. G01N 29/0681 73/618 |
| 2004/0173024 A1 | 9/2004 | McKeon |
| 2007/0012115 A1 | 1/2007 | Busch et al. |
| 2007/0180914 A1 | 8/2007 | Kessler |
| 2009/0095086 A1 | 4/2009 | Kessler et al. |
| 2009/0180931 A1 | 7/2009 | Silbert et al. |
| 2012/0125110 A1 | 5/2012 | Kessler et al. |

OTHER PUBLICATIONS

International Search Report and Written Opinion of the International Searching Authority, Application No. PCT/US2011/062116, dated Mar. 26, 2012 (11 pages).

International Search Report and Written Opinion of the International Searching Authority, Application No. PCT/US11/62101, dated Mar. 19, 2012 (8 pages).

* cited by examiner

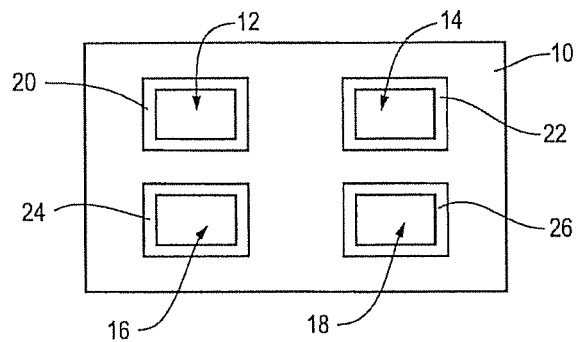
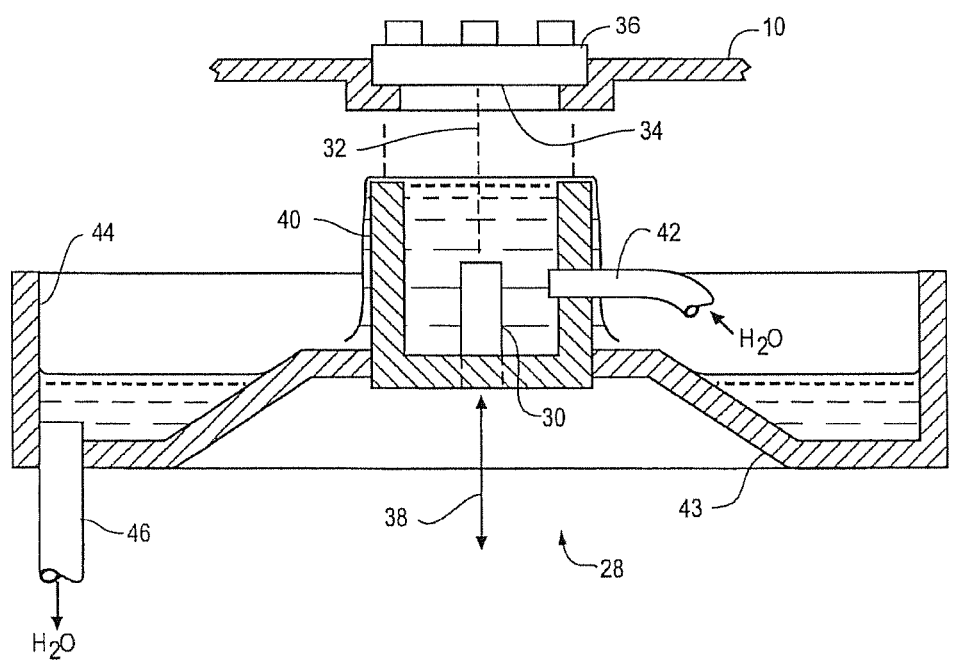

SCANNING ACOUSTIC MICROSCOPE WITH AN INVERTED TRANSDUCER AND BUBBLER FUNCTIONALITY

CROSS REFERENCE TO RELATED APPLICATIONS

This application is a continuation of U.S. patent application Ser. No. 13/304,070, filed Nov. 23, 2011, which claims the benefit of U.S. Provisional Patent Application No. 61/416,610, filed Nov. 23, 2010, which are hereby incorporated by reference herein in their entireties.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to a scanning acoustic microscope with an inverted transducer and bubbler functionality for inspecting a part.

2. Description of the Background of the Invention

U.S. Pat. No. 7,584,664 is entitled "acoustic micro imaging device having at least one balanced linear motor assembly." U.S. Pat. No. 7,522,780 is entitled "frequency domain processing of scanning acoustic imaging signals." U.S. Pat. No. 7,395,713 is entitled "tray-fed scanning microscope system and method primarily for immobilizing parts during inspection." U.S. Pat. No. 7,000,475 is entitled "acoustic micro imaging method and apparatus for capturing 4D acoustic reflection virtual samples." U.S. Pat. No. 6,981,417 is entitled "scanning acoustic micro imaging method and apparatus for non-rectangular bounded files." U.S. Pat. No. 6,895,820 is entitled "acoustic micro imaging method and apparatus for capturing 4D acoustic reflection virtual samples." U.S. Pat. No. 6,890,302 is entitled "frequency domain processing of scanning acoustic imaging signals." U.S. Pat. No. 6,880,387 is entitled "acoustic micro imaging method providing improved information derivation and visualization." U.S. Pat. No. 6,460,414 is entitled "automated acoustic micro imaging system and method." U.S. Pat. No. 6,357,136 is entitled "scanning acoustic microscope system and method for handling small parts." U.S. Pat. No. 5,684,252 is entitled "method and apparatus for ultrasonic inspection of electronic components." U.S. Pat. No. 5,600,068 is entitled "controlled-immersion inspection." U.S. Pat. No. 4,866,986 is entitled "method and system for dual phase scanning acoustic microscopy." U.S. Pat. No. 4,781,067 is entitled "balanced scanning mechanism." U.S. Pat. No. 4,518,992 is entitled "acoustic imaging system and method." U.S. Patent Application Pub. No. 20090095086 is entitled "scanning acoustic microscope with a profilometer function." U.S. Provisional Application Ser. No. 61/362,131 is entitled "acoustic micro imaging device with a scan while loading feature." The contents of all of the aforementioned patents, publications and applications are incorporated by reference into this application as if fully set forth herein.

SUMMARY OF THE INVENTION

According to one aspect, a scanning acoustic microscope includes a transducer mounted in a cup below a particular elevation capable of producing ultrasonic energy, and a coupling fluid source disposed below the particular elevation, which is configured to introduce coupling fluid into the cup. Ultrasonic energy is directed upwardly through coupling fluid disposed between and contacting the transducer and a first surface of a part to be inspected. The part is disposed at the particular elevation and a second surface of the part is not contacted by coupling fluid during testing.

According to another aspect, a scanning acoustic microscope includes a transducer mounted in a cup below a particular elevation, and a coupling fluid source disposed below the particular elevation, which is configured to introduce coupling fluid into the cup. The scanning acoustic microscope also includes a pump connected to the cup for pressurizing the coupling fluid before it enters the cup. The scanning acoustic microscope further includes a controller operable to control the transducer and the coupling fluid source during testing such that ultrasonic energy is directed upwardly through coupling fluid disposed between and contacting the transducer and a first surface of a part to be tested. The part is disposed at the particular elevation and a second surface of the part is not contacted by coupling fluid during testing.

According to yet another aspect, a method of scanning a part using a scanning acoustic microscope includes the steps of mounting a transducer mounted in a cup below a particular elevation and disposing a coupling fluid source at the particular elevation. The coupling fluid source is configured to introduce coupling fluid into the cup. The method also includes the step of providing a controller for controlling the transducer and the coupling fluid source during testing such that ultrasonic energy is directed upwardly through coupling fluid disposed between and contacting the transducer and a bottom surface of the part to be inspected. The part is disposed at the particular elevation and an upper surface of the part is not contacted by coupling fluid during testing.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein:

FIG. 1A is a top view of a tray of parts that is designed to support various large microelectronic samples for transport through a scanning acoustic microscope illustrated in the remaining figures;

FIG. 1B is a side view, partly in cross section, of a portion of an embodiment of a scanning acoustic microscope having an inverted transducer and a bubbler functionality;

DETAILED DESCRIPTION OF THE PREFERRED EMBODIMENTS

Figure 2:
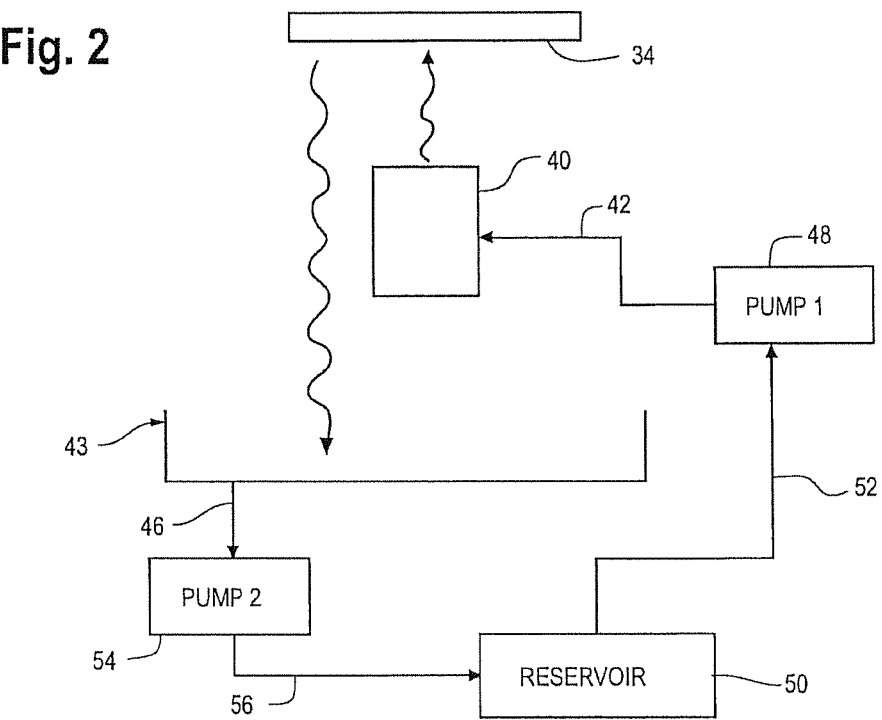
FIG. 2 is a combined diagrammatic view and block diagram showing the transport of coupling fluid through the microscope of FIG. 1B.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description of the Preferred Embodiments" relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

The description in this document concerns a scanning acoustic microscope having an inverted transducer and a bubbler feature. It is the applicants' intention to preserve the ability to claim a device that includes an inverted transducer and a bubbler feature in combination with none, any, some or all of the other acoustic microscopy features disclosed in the patents and other information incorporated by reference into this document as if fully set forth herein as noted in the background of the invention section.

FIG. 1A is a top view of a tray 10 that is designed to support a number of large microelectronic samples for transport through a scanning acoustic microscope having an inverted transducer and a bubbler feature. In the illustrated embodiment, tray 10 includes four part support areas 12, 14, 16 and 18 that are defined by ledges 20, 22, 24 and 26. A suitable target such as, for example, a microelectronic sample part 36 (shown in FIG. 1B) can be supported on the ledges 20-26 within the support areas 12-18 of the tray 10.

FIG. 1B is a side, partial cross sectional view of a portion of an embodiment of a scanning acoustic microscope 28 having an inverted transducer and a bubbler functionality. Scanning acoustic microscope 28 includes a waterproof ultrasonic transducer 30 that is designed to emit pulses of ultrasonic energy along axis 32 towards an underside 34 of a sample part 36 that, in use, is generally opposite to the force of gravity. An outer portion of sample part 36 rests on one of the ledges 20-26 defining one of the part support areas 12-18 in tray 10. Transducer 30 is connected to suitable control circuitry (not shown) via line 38.

In the illustrated embodiment of the invention, transducer 30 is secured to a bottom surface of a spray cup 40 by, for example, a threaded connection. A water inlet tube 42 is inserted through a side aperture in spray cup 40 with sufficient pressure to allow water (or any other suitable coupling fluid) to fully immerse the transducer 30 inside of spray cup 40 and then travel upwards in a laminar flow (so that bubbles or entrained air do not form in the flow, at lease until the water deflects off the part) and contact the underside 34 of sample part 36. One aspect of the invention is that, for example, the water pressure is sufficiently high to cause a water flow to cover the distance between the end of the spray cup 40 and the underside 34 of the sample part 36 without blowing the part 36 off of the tray 10 if the water pressure were too high. As discussed in greater detail hereinafter, the appropriate water pressure for a given application can be determined by visual inspection and then set and thereafter automatically applied for subsequent acoustic microscopic inspection of trays of parts as they are moved into and then out of the scanning acoustic microscope 28. Furthermore, it is may be preferable (depending upon, among other things, coupling fluid supply pressure) that a gap be maintained between the sample part 36 and the spray cup 40 to prevent water pressure from becoming too high such that the water pressure causes the part to be lifted off of the tray 10.

In addition, the sample part 36 may have a critical and non-critical side wherein the critical side cannot get wet. To prevent water from seeping up around the ledges 20-26 during the inspection of the non-critical side, a fan or air knife can be used to blow air toward the critical side of the sample part 36. The fan or air knife is preferably located above the tray 10 and scanning microscope 28 and may be of sufficient capacity to generate a stream of air that covers the entire tray 10. Alternatively, the fan or air knife may cover only a single part 36 or portion of a part, for example the edges(s) of a part 36, as desired. The fan or knife blower may also be used to maintain the sample part 36 in place if the pressure of the water flow increases.

Another feature of the invention disclosed herein involves the utilization of a drain saucer 43 that, in an exemplary embodiment of the invention, is connected to an outer and lower external surface of spray cup 40. The drain saucer 43 includes a raised outer rim 44 that is sufficiently wide to be able to capture all of the water emitted from the spray cup as it splashes off of the sample part 36 and the tray 10 and falls back towards the drain saucer 43 due to the force of gravity. A drain tube 46 is inserted in an aperture formed in a bottom portion of drain saucer 43 that is shaped so that all water caught by the drain saucer 43 is directed towards the drain tube 46.

FIG. 2 is a schematic diagram showing the transport of water through the scanning acoustic microscope 28. An inlet pump 48 draws water from reservoir 50 via tube 52, pressurizes the water to a suitable level, and then provides the pressurized water to spray cup 40 via tube 42. A drain pump 54 draws water from the drain saucer 43 via drain tube 46 and then provides the collected water back to reservoir 50 via tube 56.

Figure 3:
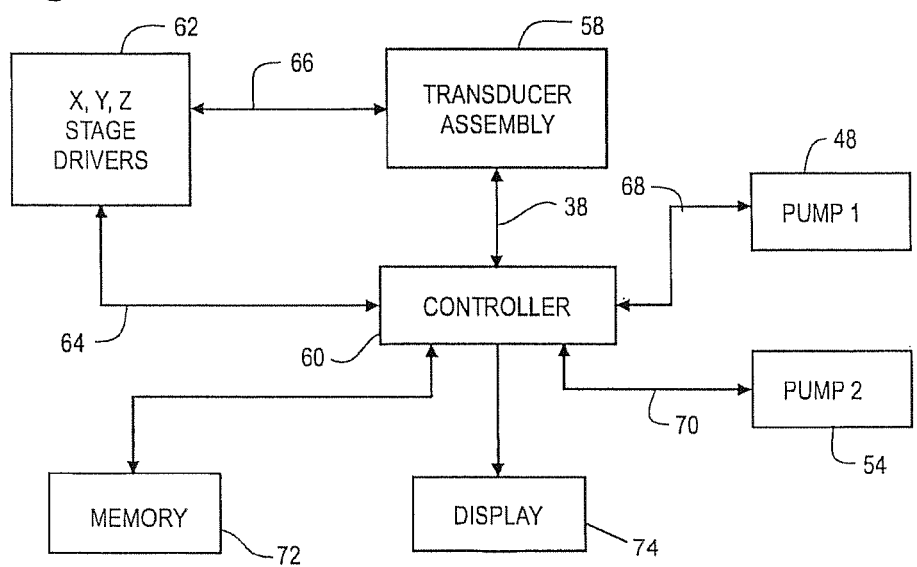
FIG. 3 is a block diagram showing the electrical connections of the microscope of FIG. 1B.

FIG. 3 is a schematic diagram showing the electrical connections of the scanning acoustic microscope 28. The transducer assembly 58 includes, in the illustrated embodiment, the transducer 30, the spray cup 40 and the drain saucer 43 shown in FIG. 1B. Electrical signals between, to, and from the transducer 30 to the controller 60 pass along line 38. Controller is electrically connected to x, y, z stage drivers 62 via line 64 so that the x, y, z stage drives can cause transducer assembly 58 to be moved in operative relation with respect to the tray 10 by means of actuators 66 to allow for non-destructive testing of the samples on tray 10 to take place. For example, this action can cause transducer 10 to be moved in an x-y raster scan of each sample.

Controller 60 also is electrically connected to pumps 48 and 54 via lines 68 and 70. The pumps 48 and 54 are turned on and off as needed for non-destructive testing purposes of samples disposed on the tray 10. Information about the scanning process and the scan results are caused to be shown on the display 74 by controller 60. For example, both time domain and frequency domain images of a particular sample can be appropriately color coded and then shown to an operator for analysis. Controller 60 is electrically connected to a memory 72 so that, if desired, data for scans can be stored for later analysis or retrieved therefrom and transmitted to others via suitable transport (e.g., email or a memory stick).

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A scanning acoustic microscope, comprising:
a transducer mounted in a cup below a particular elevation configured to produce ultrasonic energy; and
a coupling fluid source disposed below the particular elevation, which is configured to introduce coupling fluid into the cup;
wherein ultrasonic energy is directed upwardly through coupling fluid disposed between and contacting the transducer and a first surface of a part to be inspected, and
wherein the part is disposed at the particular elevation and wherein a second surface of the part is not contacted by coupling fluid during testing.

2. The scanning acoustic microscope of claim 1, further including an air source disposed above the particular elevation that is configured to blow air downwardly on the second surface of the part to be inspected to prevent the part from moving upwardly during testing.

3. The scanning acoustic microscope of claim 2, wherein the air source is a fan or air knife.

4. The scanning acoustic microscope of claim 1, further including a controller operable to control the transducer and the coupling fluid source during testing.

5. The scanning acoustic microscope of claim 1, further including a pump for pressurizing the coupling fluid before it enters the cup.

6. The scanning acoustic microscope of claim 1, further including a drain saucer proximate the cup for collecting coupling fluid.

7. The scanning acoustic microscope of claim 1, further including a driver for driving the transducer along a scan path.

8. The scanning acoustic microscope of claim 7, further including a display operated by the controller for displaying scan results.

9. A scanning acoustic microscope, comprising:
a transducer mounted in a cup below a particular elevation;
a coupling fluid source disposed below the particular elevation, which is configured to introduce coupling fluid into the cup;
a pump connected to the cup for pressurizing the coupling fluid before it enters the cup; and
a controller operable to control the transducer and the coupling fluid source during testing such that ultrasonic energy is directed upwardly through coupling fluid disposed between and contacting the transducer and a first surface of a part to be tested,
wherein the part is disposed at the particular elevation and wherein a second surface of the part is not contacted by coupling fluid during testing.

10. The scanning acoustic microscope of claim 9, further including an air source disposed above the particular elevation that is configured to blow air downwardly on the second surface of the part to prevent the part to be tested from moving upwardly during testing.

11. The scanning acoustic microscope of claim 10, wherein the air source is a fan or air knife.

12. The scanning acoustic microscope of claim 9, further including a drain saucer proximate the cup for collecting coupling fluid.

13. The scanning acoustic microscope of claim 9, further including a driver for driving the transducer along a scan path.

14. The scanning acoustic microscope of claim 9, in combination with a part to be tested, coupling fluid, and a tray that carries the part to be tested.

15. A method of scanning a part using a scanning acoustic microscope comprising the steps of:
mounting a transducer mounted in a cup below a particular elevation;
disposing a coupling fluid source at the particular elevation, wherein the coupling fluid source is configured to introduce coupling fluid into the cup; and
providing a controller for controlling the transducer and the coupling fluid source during testing such that ultrasonic energy is directed upwardly through coupling fluid disposed between and contacting the transducer and a bottom surface of the part to be inspected,
wherein the part is disposed at the particular elevation and wherein an upper surface of the part is not contacted by coupling fluid during testing.

16. The method of scanning a part of claim 15, further including the step of pressurizing the coupling fluid before it enters the cup.

17. The method of scanning a part of claim 15, further including the step of blowing air down on the part during testing.

18. The method of scanning a part of claim 15, further including the step of collecting the coupling fluid in a drain saucer disposed proximate the cup.

19. The method of scanning a part of claim 15, further including the step of driving the transducer along a scan path.

20. The method of scanning a part of claim 19, further including the step of displaying results of a scan performed on the part.

* * * * *